United States Patent [19]

Forestier et al.

[11] Patent Number: 5,102,660
[45] Date of Patent: Apr. 7, 1992

[54] POLYAMINOAMIDES WHICH FILTER ULTRAVIOLET RADIATION, PROCESS FOR THEIR PREPARATION AND THEIR USE IN THE PROTECTION OF THE SKIN AND HAIR

[75] Inventors: Serge Forestier, Claye Souilly; Gerard Lang, Saint Gratien; Edith Sainte Beuve, Survilliers, all of France

[73] Assignee: L'Oreal, Paris, France

[21] Appl. No.: 596,363

[22] Filed: Oct. 12, 1990

Related U.S. Application Data

[62] Division of Ser. No. 371,751, Jun. 27, 1989, Pat. No. 5,037,901, which is a division of Ser. No. 899,888, Aug. 25, 1986, Pat. No. 4,866,159.

[30] Foreign Application Priority Data

Aug. 30, 1985 [FR] France ................ 85 12958

[51] Int. Cl.$^5$ .............. C08L 77/06; A61K 7/42; A61K 31/765; A61K 7/06
[52] U.S. Cl. .................. 424/401; 424/59; 424/60; 424/70; 424/71; 424/72; 424/47; 424/486; 424/DIG. 1
[58] Field of Search .............. 424/401; 528/342

[56] References Cited

U.S. PATENT DOCUMENTS

| | | | |
|---|---|---|---|
| 3,395,130 | 7/1968 | Barrett et al. | 528/342 |
| 3,640,840 | 2/1972 | Zieman et al. | 528/342 |
| 4,504,644 | 3/1985 | Lang et al. | 527/201 |
| 4,689,374 | 8/1987 | Hanson et al. | 528/342 |
| 4,866,159 | 9/1989 | Forestier et al. | 528/324 |

*Primary Examiner*—Thurman K. Page
*Assistant Examiner*—E. J. Webman
*Attorney, Agent, or Firm*—Cushman, Darby & Cushman

[57] ABSTRACT

New polyaminoamides which filter ultraviolet radiation, process for their preparation and their use for protecting the skin and hair.

20 Claims, No Drawings

POLYAMINOAMIDES WHICH FILTER ULTRAVIOLET RADIATION, PROCESS FOR THEIR PREPARATION AND THEIR USE IN THE PROTECTION OF THE SKIN AND HAIR

This is a division of application Ser. No. 07/371,751, filed June 25, 1989 now U.S. Pat. No. 5,037,901 which is a division of application Ser. No. 06/899,888, filed Aug. 25, 1986, now U.S. Pat. No. 4,866,159.

The present invention relates to new polyaminoamides which filter ultraviolet radiation, to the process for their preparation and to their use in cosmetic compositions intended for protecting the skin and the hair.

It is known that light radiations of wavelengths between 280 and 400 nm allow the browning of human skin and that rays of wavelength between 280 and 320 nm known under the term UV-B also cause erythemas and cutaneous burns.

It is also known that UV-A rays of wavelength between 320 and 400 nm cause browning of the skin, but can also cause a deterioration of the latter, particularly in the case of a sensitive skin or a skin continually exposed to solar radiation. It has been found that UV-A rays can augment the action of UV-B rays as has been described by several groups of authors and more particularly by J. WILLIS, A. KLIGMAN and J. EPSTEIN (The Journal of Investigative Dermatology, Vol. 59, No. 6, page 416, 1973) under the name of Photo Augmentation. The UV-A rays promote the triggering of the erythemic reaction or amplify this reaction in some subjects. Similarly, they can be the cause of phototoxic or photo-allergic reactions. They also accelerate the aging process of the skin.

Therefore, it has appeared desirable to seek compounds which filter both UV-A and UV-B rays, with a view to protecting the skin.

Similarly, it has appeared desirable to find compounds which ensure good protection for the hair against all photochemical deterioration, especially to avoid a change of shade or a discoloration.

So-called "filter polymers" which are synthetic polymers onto which the residues of molecules which have a filtering effect towards ultraviolet radiation (French Patents Nos. 2,197,023 and 2,237,912) are grafted, are already known. The use in cosmetic compositions of such grafted synthetic polymers which filter solar radiation harmful to the skin, has the advantage, compared with the use of conventional sunlight filters such as p-aminobenzoic acid derivatives, anthranilic acid derivatives, cinnamic acid derivatives, coumarin derivatives, and the like, of avoiding or at least slowing down significantly the migration of the absorbing molecule through the skin, which eliminates the unfavourable secondary effects of sunlight filters and which makes it possible to avoid repeated applications of sunscreen compositions.

However, it was observed that these grafted synthetic polymers are generally not very soluble in common cosmetic solvents, that they form films of which the texture is too rigid and that they often have a relatively low UV radiation absorbing power, which implies that they should be used in high concentrations in the compositions which contain them.

Protein derivatives containing UV radiation-absorbing residues which are grafted onto natural polymers originating from substances of animal or vegetable origin or on protein hydrolysates are also known. These protein derivatives, which are described in French Patent Applications Nos. 2,531,960, 2,548,018 and 2,459,069, protect the skin and the hair against the undesirable effects of ultraviolet radiation.

In the course of its investigations, the Applicants have discovered new filtering polymers which have a better affinity for keratin and especially for skin and hair, than the known filtering polymers, and which have better cosmetic properties in that they spread easily and they are neither sticky nor gummy.

Moreover, these new filtering polymers have good filtering properties over a wavelength spectrum ranging from 280 to 380 nm, and are well tolerated by the skin and the hair.

Thus, the subject of the present invention is new polyaminoamides corresponding to the following general formula:

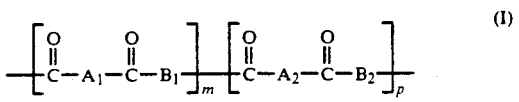

in which $A_1$ represents a divalent radical having one of the following structures:

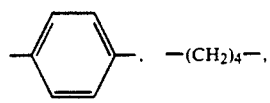

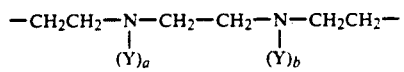

where a and b = 0 or 1

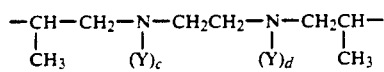

where c and d = 0 or 1

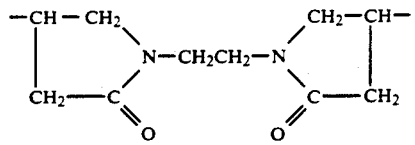

$B_1$ represents:
1) in the proportions of 60 to 100% (in moles), the radical

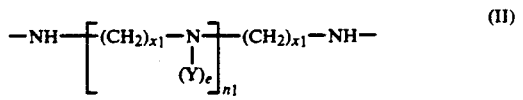

where
$x_1 = 2$ and $n_1 = 1$ or 2 or alternatively,
$x_1 = 3$ and $n_1 = 1$ and
$e = 0$ or 1
2) in the proportions of 0 to 40% (in moles), the radical (II) above in which $x_1 = 2$ and $n_1 = 0$ or the radical

3) in the proportions of 0 to 20% (in moles), the radical

in radicals $A_1$ and $B_1$, Y represents a residue of an ultraviolet radiation-absorbing molecule and $a+b+c+d+e \geq 1$, it being understood that when a, b, c, d or e are zero, the nitrogen atom is then bound to a hydrogen atom; the ratio m/p is between 0.05 and 0.5;

$A_2$ represents a divalent radical having one of the following structures:

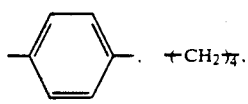

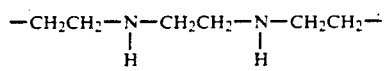

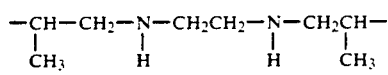

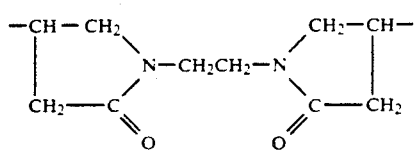

$B_2$ represents:
1) in the proportions 60 to 100% (in moles), the radical

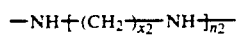 (III)

where
$x_2 = 2$ and $n_2 = 2$ or 3, or alternatively,
$x_2 = 3$ and $n_2 = 2$
2) in the proportions of 0 to 40% (in moles), the radical (III) above in which $x_2 = 2$ and $n_2 = 1$ or the radical

3) in the proportions of 0 to 20% (in moles), the radical

These filtering polyaminoamides have, in a 10% aqueous solution and at 25° C., a viscosity between 3 and 200 centipoises and preferably between 10 and 100 centipoises.

Preferably, the residue Y which represents a residue of an ultraviolet radiation-absorbing molecule belongs to a group consisting of the following radicals:

a cinnamoyl residue, optionally substituted with one or more lower alkoxy groups, a paradialkylaminobenzoyl residue;

a salicyloyl residue;

an acyl or sulphonyl residue, originating from a carboxylic or sulphonic acid, derived from benzylidenecamphor which may be optionally substituted on the aromatic ring with one or more halogen atoms, or with one or more lower alkyl or alkoxy radicals, sulphonic radical or with an alkenyl radical carrying one or more alkoxycarbonyl residues and/or optionally substituted on the carbon atom in position 10 of the camphor with a sulphonic group;

a sulphonyl residue originating from an optionally substituted iso- or terephthalylidene camphor radical;

an acyl or sulphonyl residue originating from a carboxylic or sulphonic acid, derived from a heterocyclic absorber which belongs to the group consisting of 2-arylbenzimidazoles, 2-arylbenzoxazoles, 2-arylbenzotriazoles, 2-arylbenzofurans and 2-arylindoles;

an acyl or sulphonyl residue originating from a carboxylic or sulphonic acid, derived from an absorber which belongs to the hydroxybenzophenone class;

an acyl residue derived from an absorber of coumarinic carboxylic structure, optionally substituted with one or more lower alkyl or alkoxy radicals;

an acyl residue, derived from an absorber of mono- or diphenylcyanoacrylic structure, optionally substituted on the aromatic ring(s);

an acyl or sulphonyl residue, derived from an absorber of dibenzoylmethane structure, optionally substituted with one or more hydroxyl, lower alkoxy or alkyl radicals.

By lower alkyl or alkoxy residues is understood residues containing 1 to 6 carbon atoms.

It is especially preferred that the group Y of the compound of formula (I) belongs to the group consisting of the following radicals:

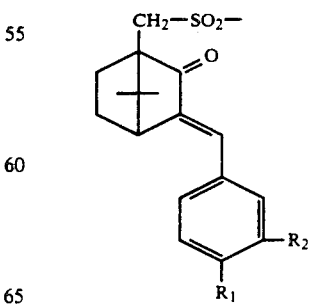

(with $R_1$ = H, $CH_3$, Cl or O-alkyl
$R_2$ = H, O-alkyl)

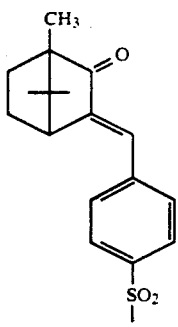

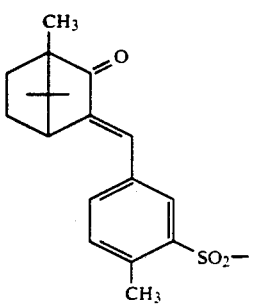

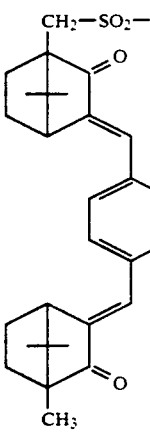

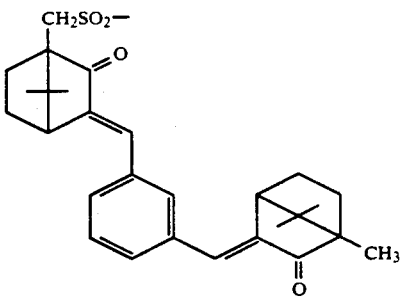

The present invention also relates to a process for the preparation of the polyaminoamides of formula (I) which consists in condensing one or more compounds of formula (IV) with a diaminoamide of formula (V) according to the reaction scheme below:

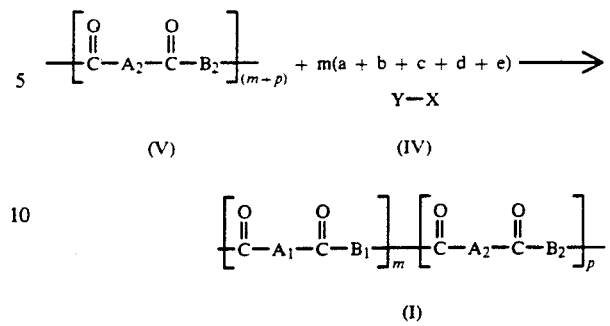

In formulae (IV) and (V), $A_2$, $B_2$, Y, m, p, a, b, c, d and e have the meanings given above for the polymers of formula (I), and X represents a halogen atom.

The polyaminoamides of formula (V) are obtained according to the process described in French Patent No. 2,252,840 of the Applicants.

The polyaminoamides of general formula (V) may, if required, be crosslinked by the addition of a cross-linking agent. A bifunctional compound chosen from (a) epihalohydrins, for example, epichlorhydrin;

(b) diepoxides, for example diglycidyl ether, N,N'-bis-epoxypropylpiperazine;

(c) dianhydrides, for example, butanetetracarboxylic acid dianhydride, pyromellitic acid dianhydride;

(d) bis-unsaturated derivatives, for example, divinylsulphone, methylene bis-acrylamide, are used as a crosslinking agent.

This crosslinking may be carried out according to the conditions described in French Patent No. 2,252,840.

The condensation of the compounds of formula (IV) with the polyaminoamide of formula (V) is an acylation reaction which is carried out in the conventional way by means of an acid halide in an alkaline medium.

The compounds (I) of the invention filter solar radiation over a wavelength region which is a function of the nature of the filter grafted onto the polyaminoamide.

Thus, when Y- represents a cinnamoyl residue, optionally substituted with one or more alkoxy group(s), a p-dialkylaminobenzoyl residue, a salicyloyl residue, an acyl residue originating from a carboxylic or sulphonic acid derived from benzylidenecamphor, a sulphonyl residue originating from an isophthalylidenecamphor, an acyl residue originating from a carboxylic or sulphonic acid derived from 2-arylbenzimidazoles, 2-arylbenzoxazoles, 2-arylbenzotriazoles, 2-arylbenzofurans, 2-arylindoles, hydroxybenzophenones or an acyl residue derived from an absorber of coumarinic carboxylic structure, the compounds generally absorb over a wavelength region between 280 and 320 nm, corresponding to the UV-B.

When Y- represents a sulphonyl residue originating from a terephthalylidenecamphor, a sulphonyl residue derived from benzylidenecamphor, substituted on the aromatic ring with one or more lower alkoxy radicals, an acyl residue originating from a carboxylic or sulphonic acid derived from 2-arylbenzotriazoles, from hydroxybenzophenones or an acyl residue derived from an absorber of mono- or diphenylcyanoacrylic structure, the compounds generally absorb over a wavelength region between 320 and 380 nm corresponding to UV-A.

When Y- represents an acyl residue derived from an absorber of an optionally substituted dibenzoylmethane structure, the compounds generally absorb over a wavelength region between 320 and 380 nm.

The present invention also relates to a cosmetic composition containing, in a cosmetically acceptable carrier, an effective amount of at least one compound of formula (I) and which can be used as a composition which protects human skin or as a sunscreen composition.

The invention also relates to a composition for the treatment and the protection against UV rays of natural or sensitized hair, which composition contains, in a cosmetically acceptable carrier, an effective amount of at least one compound of formula (I). The term "sensitized hair" refers to hair which has been subjected to a permanent waving, dyeing or bleaching treatment.

The cosmetic composition according to the invention which protects the skin or hair contains 0.5 to 15% by weight of at least one compound of the formula (I).

The compound(s) or formula (I) is (are) solubilized in a solvent chosen from the group consisting of water, lower monohydric or polyhydric alcohols containing 1 to 6 carbon atoms and aqueous/alcoholic solutions. The monohydric or polyhydric alcohols which are more particularly preferred are chosen from: ethanol, isopropanol, propylene glycol, glycerol, sorbitol; the aqueous-/alcoholic solutions are preferably mixtures of water and ethanol.

The compositions according to the invention may be in various forms which are commonly used for this type of composition. They may especially be present in solution in the form of a more or less thickened lotion, in emulsion in the form of a cream or a milk, in the form of a gel, or may be packaged as an aerosol.

The compositions intended for protecting the skin, which constitute one object of the present invention, may contain cosmetic adjuvants which are commonly used in this type of compositions such as fatty substances, for example mineral, animal or vegetable oils or waxes, fatty acids, fatty acid esters such as fatty acid triglycerides containing from 6 to 12 carbon atoms and fatty alcohols.

Among the mineral oils, vaseline oil may be mentioned; among the animal oils, whale, seal, menhaden, halibut liver, cod, tuna, turtle, tallow, neat's-foot, horse foot, sheep's-foot, mink, otter and marmot oils may be mentioned; among vegetable oils, almond, peanut, wheatgerm, olive, corn, jojoba, sesame, sunflower, palm and walnut oils may be mentioned.

Among the fatty acid esters, isopropyl esters of myristic, palmitic and stearic acids and fatty esters which are solid at 25° C. may be mentioned.

As fatty substances, vaseline, paraffin, lanolin, hydrogenated lanolin, acetylated lanolin and silicone oils may also be mentioned.

Among waxes, Sipol wax, Lanolin wax, beeswax, candelilla wax, microcrystalline wax, carnauba wax, speraceti, cocoa butter, karite butter, silicone waxes, hydrogenated oils solid at 25° C., sugar glyceride and Ca, Mg, Zn and Al oleates, myristates, linoleates and stearates may be mentioned.

Among fatty alcohols, lauryl, cetyl, myristyl, stearyl, palmityl, oleyl alcohols may be mentioned.

The cosmetic composition may also contain emulsifiers which may be nonionic, anionic, cationic or amphoteric.

It may also be useful to use thickeners such as cellulose derivatives, derivatives of polyacrylic acid crosslinked with a polyfunctional agent, guar or carob gums.

The cosmetic composition according to the invention for the protection of skin may also contain other adjuvants which are commonly used in cosmetics and especially moisturizing products, softeners, preservatives, opacifiers, antifoams, perfumes, colorants, and/or pigments intended to colour the composition itself or the skin, or any other ingredient usually employed in cosmetics.

In the case of a composition which is packaged as an aerosol, conventional propellants such as alkanes, fluoroalkanes and chlorofluoroalkanes are employed.

An embodiment of the composition which protects the human skin is an emulsion in the form of a protective cream or milk containing, in addition to the compound of formula (I), the fatty substances mentioned above and emulsifiers, in the presence of water.

Another embodiment consists of lotions such as oil-alcohol lotions based on lower alcohols such as ethanol, or glycols such as propylene glycol and/or polyhydric alcohols such as glycerine, and fatty acid esters such as fatty acid triglycerides.

Aqueous alcoholic lotions based on lower alcohols, glycols or polyhydric alcohols mentioned above and water may also be cited.

The cosmetic composition which protects human skin according to the invention may also be an oil-alcoholic gel containing one or more lower alcohols, glycols or polyhydric alcohols such as ethanol, propylene glycol or glycerine and a thickener, in the presence of oil. The alcoholic or aqueous alcoholic gels contain one or more lower alcohols, glycols or polyhydric alcohols mentioned above and thickener in the presence of water.

When the compositions protecting the human skin according to the invention are used as sunscreen compositions, they contain at least one compound of formula (I) which may optionally be combined with one or more other sunlight filters which are specific to UV-B radiation or to UV-A radiation and which are compatible with the compound according to the invention. It is therefore possible to obtain a formulation which filters all of the UV-B and UV-A rays.

The compounds (I) according to the invention may be combined with UV-B filters formed by liposoluble compounds or by oils which have filtering properties such as, in particular, coffee oil. By way of lipophilic UV-B sunlight filters, there may be mentioned salicylic acid derivatives such as 2-ethylhexyl salicylate, homomenthyl salicylate, cinnamic acid derivatives such as 2-ethylhexyl p-methoxycinnamate, 2-ethoxyethyl p-methoxycinnamate, aminobenzoic acid derivatives such as amyl p-aminobenzoate, 2-ethylhexyl p-dimethylaminobenzoate, benzophenone derivatives such as 2-hydroxy-4-methoxybenzophenone, 2,2'-dihydroxy-4-methoxybenzophenone, camphor derivatives such as 3-(4'-methylbenzylidene)camphor, if desired, in combination with 4-isopropyldibenzoylmethane or 3-benzylidenecamphor.

By way of water-soluble sunlight filters which filter UV-B rays which may also be combined with the filters according to the invention, provided they are compatible with the latter, there may be mentioned the benzylidenecamphor derivatives described in French Patent Nos. 2,199,971 and 2,383,904 of the Applicants and, more particularly, 4-(2-oxo-3-bornylidenemethyl)-phenyltrimethylammonium methyl sulphate.

The compounds according to the invention may also be combined with UV-A filters, among which dibenzoylmethane derivatives may be mentioned.

It is to be understood that the list of sunlight filters employed in combination with the filters according to the invention which is given above is not limitative.

Another subject of the invention consists of compositions intended for protecting natural or sensitized hair or for treating them.

These compositions may be present in the form of shampoos, rinse-off lotions, gels or emulsions to be applied before or after shampooing, before or after dyeing or bleaching, before or after permanent waving, styling or treating lotions or gels, lotions or gels for blow-drying or wave-setting or in the form of hair lacquers. These compositions may contain, in addition to the compound of formula (I), various adjuvants which are commonly used in this type of composition, such as surfactants, thickeners, polymers, softeners, preservatives, foam stabilizers, electrolytes, organic solvents, silicone derivatives, oils, pH-regulating agents, waxes, anti-grease agents, colorants, and/or pigments intended for colouring the composition itself or the hair and any other ingredient which is commonly used in the field of hair care.

When the compositions constitute shampoos, the latter are essentially characterized in that they contain at least one anionic, nonionic or amphoteric surfactant or mixture thereof and a compound of formula (I), in an aqueous medium. The shampoos may also contain different adjuvants such as cationic surfactants, colorants, preservatives, thickeners, foam stabilizing agents, synergistic agents, softeners, electrolytes, sequestering agents, one or more cosmetic resins, perfumes, natural substances, oils and any other adjuvant used in a shampoo. In these shampoos, the concentration of the surfactant is generally between 2 and 50% by weight.

Among the nonionic surfactants, there may be mentioned, in particular: condensation products of a monohydric alcohol, an α-diol, an alkylphenol, an amide or a diglycolamide with glycidol, such as, for example, the nonionic surfactants described in French Patents 2,091,516, 2,328,763, 1,477,048; as well as the polyoxyethylenated or polyglycerolated fatty acids, alkylphenyls or alcohols with a fatty acid chain containing 8 to 18 carbon atoms and most frequently containing 2 to 30 moles of ethylene oxide or 1 to 10 moles of glycidol, copolymers of ethylene oxide and propylene oxide, condensates of ethylene oxide and propylene oxide with fatty alcohols, polyoxyethylenated fatty amides, polyoxyethylenated fatty amines, ethanolamides, fatty acid esters of glycol, fatty acid esters of sorbitol, fatty acid esters of sucrose and glycoside alkyl ethers.

The anionic surfactants which may be used optionally in mixtures with nonionic surfactants are chosen especially from the alkali metals, the ammonium salts, the amine salts or the amino alcohol salts of the following compounds:

alkyl sulphates, alkyl ether sulphates, alkylamide sulphates and alkylamide ether sulphates, alkylarylpolyether sulphates and monoglyceride sulphates;

alkylsulphonates, alkylamide sulphonates, alkylarylsulphonates, α-olefin sulphonates, alkyl sulphosuccinates, alkyl ether sulphosuccinates and alkylamide sulphosuccinates, alkyl sulphosuccinamates, alkyl sulphoacetates, alkyl polyglycerol carboxylates, alkyl phosphates and alkyl ether phosphates, acylsarcosinates, acylpolypeptidates, acylamidopolypeptidates, acylisethionates and acyltaurates, the alkyl and acyl radicals in all these compounds containing 12 to 18 carbon atoms, fatty acids such as oleic acid, ricinoleic acid, palmitic acid, stearic acid and acids derived from coconut oil or hydrogenated coconut oil, carboxylic acids of polyglycol ethers corresponding to the formula:

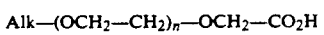

$$Alk-(OCH_2-CH_2)_n-OCH_2-CO_2H$$

in which the substituent Alk corresponds to a straight chain containing 12 to 18 carbon atoms and in which n is an integer between 5 and 15.

It is also possible to use any other anionic surfactant not mentioned above, which is well-known in the prior art.

Among the amphoteric surfactants which may be used there may be mentioned, more particularly, alkylamino monopropionates and dipropionates, betaines such as N-alkylbetaines, N-alkylsulphobetaines, N-alkylamidobetaines, cycloimidinium compounds such as alkylimidazolines, and asparagine derivatives. The alkyl group in these surfactants preferably contains not more than 22 carbon atoms.

When the compositions constitute unrinsed lotions—blow-drying lotions, wave-setting lotions, styling or treating lotions—they contain, generally in an aqueous, alcoholic or aqueous/alcoholic solution, in addition to the compound of formula (I), at least one cationic, anionic, nonionic or amphoteric polymer or a mixture thereof in quantities generally of between 0.1 and 10%, and preferably, between 0.1 and 3% by weight, and, if required, antifoaming agents.

When the compositions constitute rinsed solutions, also called rinses, they are applied before or after dyeing, before or after permanent waving before or after shampooing or between two shampooings, and then rinsed after a rest period.

These compositions may be aqueous, alcoholic or aqueous/alcoholic solutions containing, if required, surfactants, emulsions or gels. These compositions may also be pressurized as aerosols.

The surfactants which may be used in solutions are essentially nonionic or cationic surfactants of the type of those described above for the shampoo compositions and in particular condensatior products of a monohydric alcohol, and α-diol, an alkylphenol, an amide or a diglycolamide with glycidol.

It is also possible to use polyoxyethylenated or polyglycerolated fatty acids, alkylphenols or alcohols with a fatty chain containing between 8 and 18 carbon atoms and most often containing 2 to 15 moles of ethylene oxide or 1 to 5 moles of glycidol. The concentration of surfactants may vary between 0.1 and 10%, and preferably between 0.5 and 7% by weight.

It is possible to add to these compositions in the form of solutions, nonionic, cationic, anionic or amphoteric polymers and, if required anionic or amphoteric surfactants.

When the compositions are in the form of an emulsion, they mainly consist of a mixture of oils and/or fatty alcohols and polyoxyethylenated fatty alcohols such as polyoxyethylenated stearyl or cetylstearyl alcohols in the presence of water. It is possible to add to these emulsions cationic surfactants or cationic polymers.

When the compositions are in the form of a gel, they contain thickeners in the presence or absence of solvents. The thickeners which may be used can be: sodium alginate or gum arabic or cellulose derivatives such as methylcellulose, hydroxymethylcellulose, hydroxyethylcellulose, or hydroxypropylcellulose. The lotions may also be thickened with a mixtures of polyethylene glycol and polyethylene glycol stearate or distearate or with a mixture of phosphoric acid esters and amides. The concentration of thickeners may vary from 0.1 to 30%, and preferably, from 0.5 to 15% by weight.

The present invention also relates to a process for the protection of the skin and the hair against UV rays, consisting in applying to the latter an effective amount of a cosmetic composition as defined above.

The following examples illustrate the invention without limiting it.

EXAMPLES OF PREPARATION

EXAMPLE 1

Preparation of a compound of formula:

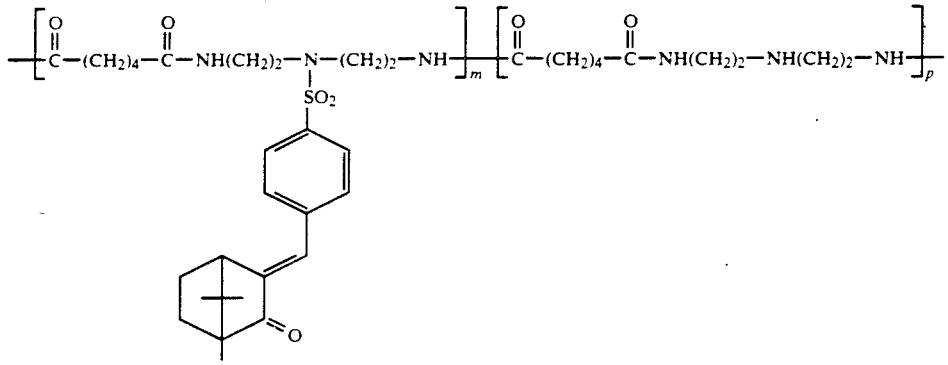

in which $m/p = 0.077$

This compound is crosslinked in the proportion of 11 moles of epichlorhydrin per 100 secondary amine groups of the polyaminoamide.

100 cm³ of a 20% strength aqueous solution of the polyaminoamide obtained by the condensation of adipic acid and diethylenetriamine are introduced into a 500-cm³ reactor, according to the operating conditions described in Example I of French Patent No. 2,252,840. This polyaminoamide is crosslinked in the proportion of 11 moles of epichlorhydrine per 100 secondary amine groups, as described in Example Ia of the abovementioned French patent.

100 cm³ of acetone are added. 8 g of 3-(4'-chlorosulphonylbenzylidene) camphor are introduced in the course of 50 minutes and at a temperature of approximately 40° C. Throughout the period of addition, the pH of the reaction mixture is maintained between 8.5 and 8.75 by the addition of an aqueous 4N sodium hydroxide solution. After the completion of the introduction, the mixture is maintained stirred for 1 hour at 40° C. The reaction mixture is filtered and the filtrate is adjusted to pH 6.8 by the addition of hydrochloric acid. The solution is poured into 1.5 litres of acetone. The gummy precipitate is washed with acetone and then redissolved in water and freeze-dried.

19 g of the expected product containing approximately 17% by weight of the grafted filter, are thereby obtained.

A 10% aqueous solution has a viscosity of 40 cP at 25° C.

UV spectrum: (water)
$\lambda_{max} = 298$ nm

E 1% = 153
E 1% represents the optical density determined at the wavelength of maximum absorption using an aqueous solution containing 1% by weight of the filtering compound.

Ungrafted filter content: less than 0.02%, determined by HPLC.

EXAMPLE 2

Preparation of a compound of formula:

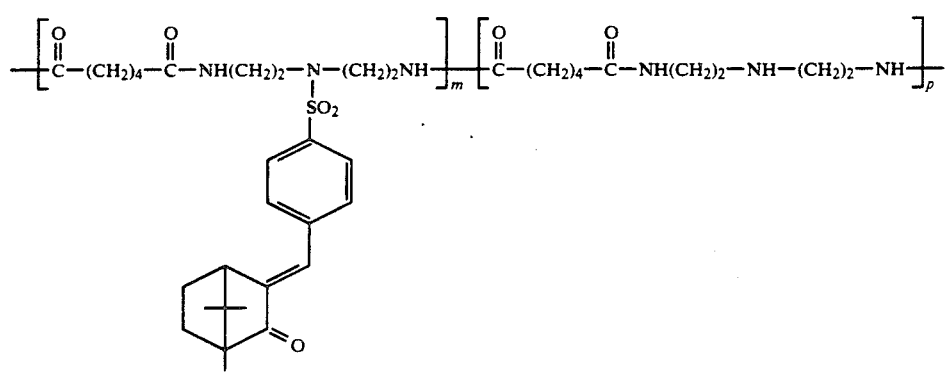

in which $m/p = 0.12$

This compound is obtained according to the procedure described in Example 1 using 5.25 g of 3-(4′chlorosulphonylbenzylidene)camphor.

18 g of the expected product containing approximately 28% of the grafted filter, are obtained.

UV spectrum: (water) λmax=296 nm
E 1% = 244

Ungrafted filter content: less than 0.02%, determined by HPLC.

EXAMPLES OF APPLICATION

EXAMPLE 1

| Shampoo | AS concentration |
|---|---|
| Compound of Example 1 | 1.2 g |
| Sodium lauryl ether sulphate with 2 moles of ethylene oxide, sold at 25% AS* | 5 g |
| Alkyl (C$_{12}$-C$_{18}$) dimethylcarboxymethylammonium hydroxide, sold under the name "Dehyton AB 30" by HENKEL at an AS concentration of 30% | 3 g |
| Sodium hydroxide q.s. pH = 8 | |
| Water q.s. | 100 g |

*AS: active substance

EXAMPLE 2

| Shampoo | AS concentration |
|---|---|
| Compound of Example 2 | 0.5 g |
| Ammonium lauryl sulphate at 30% AS | 6 g |
| Potassium salt of the condensation product of coconut fatty acids and collagen polypeptides, sold under the name "Lamepon S" by GRUNAU at an AS concentration of 33% | 4 g |
| Hydrochloric acid q.s. pH = 6 | |
| Water q.s. | 100 g |

EXAMPLE 3

| Post-shampoo treatment | AS concentration |
|---|---|
| Compound of Example 1 | 1.5 g |
| Mixture of stearyl alcohol and cetyl stearyl alcohol containing 15 moles of ethylene oxide | 2 g |
| Hydroxyethylcellulose, sold under the name "Cellosize QP 4400 H" by UNION CARBIDE | 2.5 g |
| Cetyltrimethylammonium bromide, (cetrimonium bromide, CTFA designation) | 0.4 g |
| Hydrochloric acid q.s. pH = 5 | 5 |
| Water q.s. | 100 g |

EXAMPLE 4

| Post-shampoo treatment | AS concentration |
|---|---|
| Compound of Example 2 | 0.8 g |
| Sodium chloride | 4 g |
| Heteropolysaccharide sold under the name "Actigum C × 9" by CECA | 1 g |
| Quaternary cellulose sold under the name "JR 400" by UNION CARBIDE | 0.5 g |
| Sodium hydroxide q.s. pH = 7 | |

| Post-shampoo treatment | AS concentration |
|---|---|
| Water q.s. | 100 g |

EXAMPLE 5

| Rinsed Lotion | |
|---|---|
| Compound of Example 1 | 3 g AS |
| Sodium hydroxide q.s. pH = 7 | |
| Water q.s. | 100 g |

This rinsed lotion, applied after shampooing, has a protecting effect against light.

EXAMPLE 6

| Cream | |
|---|---|
| Compound of Example 2 | 4 g |
| Glycerine | 10 g |
| Oxyethylenated stearyl alcohol, sold under the name "Polawax GP200" (CRODA) | 4 g |
| Isopropyl palmitate | 4 g |
| Stearyl alcohol | 2 g |
| Isopropyl myristate | 2 g |
| Perfume | 0.4 g |
| Demineralized water q.s. | 100 g |

This cream is applied on clean and wet hair, and is allowed to set for a few minutes, and the hair is rinsed and then dried. The hair is protected from light.

EXAMPLE 7

| Cream | |
|---|---|
| Compound of Example 1 | 8 g |
| Isopropyl myristate | 15 g |
| Glycerine | 15 g |
| Mixture of glyceryl stearate and polyethylene glycol stearate, sold under the name "ARLACEL 165" (ATLAS) | 8 g |
| Stearyl alcohol | 6 g |
| Preservative | 0.2 g |
| Perfume | 0.2 g |
| Demineralized water q.s. | 100 g |

This cream is applied to the hair in the same way as in Example 6.

EXAMPLE 8

| Sunscream cream for the skin | |
|---|---|
| Compound of Example 1 | 5 g |
| 4-[(2-Oxo-3-bornylidene)methyl]phenyl-trimethylammonium methyl sulphate | 3 g |
| Liquid paraffin | 17 g |
| Cetyl alcohol | 7.5 g |
| Uncrystallizable 70% sorbitol (DUMONT COIFFARD) | 5 g |
| Methylglucose sesquistearate, sold under the name "GLUCATE SS" (AMERCHOL) | 4.5 g |
| Sodium lactate | 0.75 g |
| Methylglucose (20 units of ethylene oxide) sesquistearate, sold under the name GLUCAMATE SSE 20 (AMERCHOL) | 0.3 g |
| Perfume | 0.4 g |
| Demineralized water q.s. | 100 g |

EXAMPLE 9

| Sunscreen cream for the skin | |
|---|---|
| Compound of Example 1 | 5 g |
| Compound of Example 2 | 4 g |
| 2-Hydroxy-4-methoxybenzophenone, sold under the name "UVINUM 40" (BASF-WYANDOTTE) | 2 g |
| 4-Methoxy-4'-tert-butyldibenzoyl-methane, sold under the name "PARSOL 1789" (GIVAUDAN) | 1 g |
| Liquid paraffin | 20 g |
| Sorbitan monoisostearate, sold under the name CRILL 6 (CRODA) | 6 g |
| Hydroxyoctacosanyl hydroxystearate, sold under the name ELFACOS C 26 (AKZO) | 3.5 g |
| Paraffin 50/52° | 1 g |
| Beeswax | 2 g |
| Dihydrated dipotassium salt of ethylenediaminetetraacetic acid | 0.1 g |
| Methyl parahydroxybenzoate | 0.1 g |
| Perfume | 0.3 g |
| Propyl parahydroxybenzoate | 0.1 g |
| Butyl hydroxytoluene | 0.05 g |
| Demineralized water q.s. | 100 g |

EXAMPLE 10

| Sunscreen milk | |
|---|---|
| Compound of Example 1 | 4 g |
| Benzylidenecamphor | 2.5 g |
| Liquid paraffin | 10 g |
| Isopropyl palmitate | 6 g |
| Cetyl alcohol | 4.5 g |
| Sorbitan stearate, sold under the name ARLACEL 60 (ATLAS) | 3 g |
| Mixture of sorbitol monostearate and sorbitol oxyethylenated with 20 moles of ethylene oxide, sold under the name TWEEN 60 (ATLAS) | 4 g |
| Preservative | 0.2 g |
| Perfume | 0.4 g |
| Demineralized water q.s. | 100 g |

We claim:

1. A composition for application to the hair or skin so as to protect said skin and hair against ultraviolet radiation, said composition comprising in a carrier suitable for application to the hair or skin an effective amount for protecting hair or skin of at least one polyaminoamide having recurring units of the formula $$\left(\begin{matrix}O & O \\ \| & \| \\ C-A_1-C-B_1\end{matrix}\right)_m \left(\begin{matrix}O & O \\ \| & \| \\ C-A_2-C-B_2\end{matrix}\right)_p$$

wherein
$A_1$ represents a divalent radical having one of the following structures:

—C$_6$H$_4$— , —(CH$_2$)$_4$—, $$-CH_2-CH_2-\underset{(Y)_a}{N}-CH_2-CH_2-\underset{(Y)_b}{N}-CH_2-CH_2-$$

wherein a and b are 0 or 1, $$-\underset{CH_3}{CH}-CH_2-\underset{(Y)_c}{N}-CH_2-CH_2-\underset{(Y)_d}{N}-CH_2-\underset{CH_3}{CH}-,$$

wherein c and d are 0 or 1, and $$-\underset{CH_2-C}{\overset{-CH-CH_2}{|}}\underset{\underset{O}{\|}}{N}-CH_2-CH_2-\underset{\underset{O}{\|}}{N}\underset{C-CH_2}{\overset{CH_2-CH-}{|}}$$

$B_1$ represents:
(1) in an amount of 60 to 100 molar percent the radical $$-NH-\left[(CH_2)_{x1}-\underset{(Y)_e}{N}-\right]_{n1}(CH_2)_{x1}-NH- \quad (II)$$

wherein $x_1$ is 2 and $n_1$ is 1 or 2, or alternatively, $x_1$ is 3 and $n_1$ is 1, and e is 0 or 1, (2) in an amount of 0 to 40 molar percent, the said radical (II) wherein $x_1$ is 2 and $n_1$ is 0 or the radical, $$-N\underset{\phantom{aa}}{\overset{\phantom{aa}}{\diagup\!\!\diagdown}}N-,$$

(3) in an amount of 0 to 20 molar percent the radical, —NH—(CH$_2$)$_6$—NH—,

Y, in $A_1$ and $B_1$, represents the residue of an ultraviolet radiation-absorbing molecule absorbing UV radiation in the range of 280–380 nm, and $a+b+c+d+e$ is equal to or greater than 1 with the proviso that when a, b, c, d or e are zero, the nitrogen atom is then bound to a hydrogen atom;

$A_2$ represents a divalent radical having one of the following structures:

—C$_6$H$_4$— , —(CH$_2$)$_4$—, $$-CH_2-CH_2-\underset{H}{N}-CH_2-CH_2-\underset{H}{N}-CH_2-CH_2-,$$

$$-\underset{CH_3}{CH}-CH_2-\underset{H}{N}-CH_2-CH_2-\underset{H}{N}-CH_2-\underset{CH_3}{CH}- \text{ or}$$

$$-\underset{CH_2-C}{\overset{-CH-CH_2}{|}}\underset{\underset{O}{\|}}{N}-CH_2-CH_2-\underset{\underset{O}{\|}}{N}\underset{C-CH_2}{\overset{CH_2-CH-}{|}},$$

$B_2$ represents:
(1) in an amount of 60 to 100 molar percent, the radical, —NH((CH$_2$)$_{x2}$—NH)$_{n2}$ (III) wherein $x_2$ is 2 and $n_2$ is 2 or 3, or alternatively, $x_2$ is 3 and $n_2$ is 2, (2) in an amount of 0 to 40 molar percent, the said radical (III) wherein $x_2$ is 2 and $n_2$ is 1 or the radical,

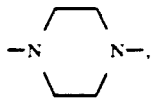

(3) in an amount of 0 to 20 molar percent the radical, $-NH-(CH_2)_6-NH-$, and the ratio, m/p, being between 0.05 and 0.5, such that said polyamino amide in a 10 percent aqueous solution has a viscosity ranging from 3–200 centipoises at 25° C.

2. The composition of claim 1 wherein said polyaminoamide is crosslinked with an epihalohydrin, a diepoxide, a dianhydride or a bis unsaturated derivative.

3. The composition of claim 1 where in said polyamino amide Y is selected from the group consisting of
   (1) a cinnamoyl radical, unsubstituted or substituted with at least one alkoxy group,
   (2) a paradialkylaminobenzoyl radical,
   (3) a salicyloyl radical,
   (4) an acyl or sulphonyl radical of a benzylidene camphor carboxylic or sulphonic acid unsubstituted or substituted on the aromatic ring with at least one halogen, lower alkyl, alkoxy, sulphonic radical or alkenyl substituted with at least one alkoxycarbonyl, or substituted on the carbon atom in position 10 of the camphor moiety with a sulphonic group,
   (5) a sulphonyl radical of an unsubstituted or substituted iso- or terephthalylidene camphor radical,
   (6) an acyl or sulphonyl radical of a heterocyclic carboxylic or sulphonic acid absorber which belongs to the group consisting of 2-arylbenzimidazole, 2-arylbenzoxazole, 2-arylbenzotriazole, 2-arylbenzofuran and 2-arylindole,
   (7) an acyl or sulphonyl radical of a carboxylic or sulphonic acid absorber of the hydroxybenzophenone class,
   (8) an acyl radical of an absorber having a coumarinic carboxylic structure, unsubstituted or substituted with at least one lower alkyl or alkoxy radical,
   (9) an acyl radical of an absorber having a mono- or diphenylcyanoacrylic structure, unsubstituted or substituted on an aromatic ring thereof and
   (10) an acyl or sulphonyl radical of an absorber having a dibenzoylmethane structure, unsubstituted or substituted with at least one hydroxyl, lower alkoxy or alkyl radical.

4. The composition of claim 1 wherein said polyaminoamide Y is selected from the group consisting of

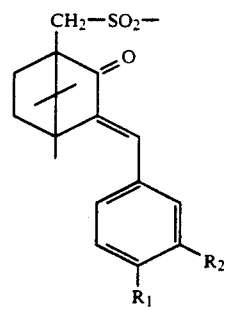

wherein $R_1$ is H, $CH_3$, Cl or O-alkyl and $R_2$ is H or O-alkyl,

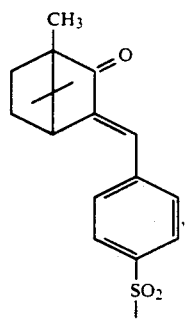

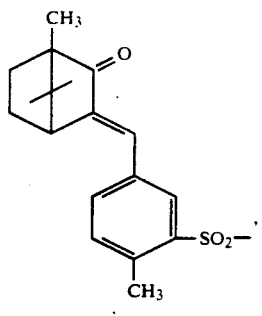

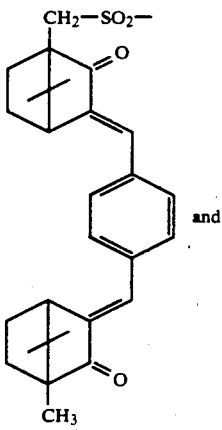

and

-continued

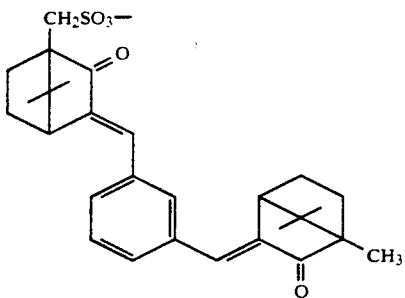

5. The composition of claim 1 wherein said polyaminoamide has recurring units of the formula

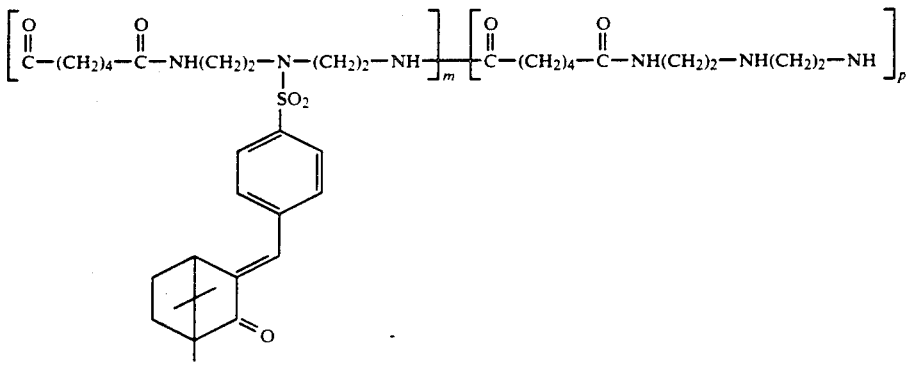

wherein the ratio m/p is 0.077, a 10 percent aqueous solution of said polyaminoamide having a viscosity of 40 centipoises at 25° C.

6. The composition of claim 1 wherein said polyaminoamide is present in an amount ranging from 0.5 to 15 percent by weight based on the total weight of said composition.

7. The composition of claim 1 wherein said polyaminoamide is dissolved in a solvent selected from the group consisting of water, a lower monohydric alcohol, a polyhydric alcohol containing 1 to 6 carbon atoms and an aqueous alcoholic solution.

8. The composition of claim 1 which also includes at least one adjuvant selected from the group consisting of a fatty substance, an emulsifier, a thickener, a moisturizing product, a softener, a colorant, a pigment, an opacifier, a preservative, a perfume and an antifoam agent.

9. The composition of claim 8 wherein said fatty substance is selected from the group consisting of a mineral oil, an animal oil, a vegetable oil, a mineral wax, an animal wax, a vegetable wax, a fatty acid, a fatty acid ester, a fatty triglyceride containing 6 to 12 carbon atoms and a fatty alcohol.

10. The composition of claim 8 which is a solution in the form of an oil-alcoholic lotion, an aqueous alcoholic lotion, an emulsion in the form of a cream or a milk, an oil-alcoholic gel, an alcoholic gel, an aqueous alcoholic gel, or a packaged aerosol.

11. The composition of claim 8 which also contains, in addition to the polyaminoamide of formula (I), at least one other sunlight filter which is specific for UV-B radiation or UV-A radiation and which is compatible with said polyaminoamide of formula (I).

12. The composition of claim 1 which is in the form of a shampoo; a lotion, gel or emulsion to be applied before or after a shampoo, before or after dyeing or bleaching the hair or before or after permanent waving the hair; a hair styling or treating lotion or gel; a hair blow-drying or hair wave-setting lotion or gel; or a hair lacquer.

13. The composition of claim 12 which also includes at least one adjuvant selected from the group consisting of a surfactant, a thickener, a polymer, a softener, a preservative, a foam stabilizer, an electrolyte, an organic solvent, an oil, a wax, an anti-grease agent, a pH regulating agent, a colorant and a pigment.

14. The composition of claim 12 in the form of a shampoo, said composition also containing an anionic, nonionic or amphoteric surfactant or a mixture thereof, said surfactant being present in an amount ranging from 2 to 50 weight percent based on the total weight of said composition.

15. The composition of claim 12 in the form of an unrinsed lotion containing in an aqueous, alcoholic or aqueous alcoholic solution, a cationic, anionic, nonionic or amphoteric polymer or a mixture thereof, said polymer or mixture thereof being present in an amount ranging from 0.1 to 10 percent by weight based on the total weight of said composition.

16. The composition of claim 15 wherein said polymer or mixture thereof is present in an amount ranging from 0.1 to 3 percent by weight based on the total weight of said composition.

17. The composition of claim 12 in the form of a rinsed lotion containing in an aqueous, alcoholic or aqueous alcoholic solution a nonionic or cationic surfactant.

18. The composition of claim 12 in the form of a rinsed emulsion containing (i) a mixture of an oil and a polyoxyethylenated fatty alcohol, (ii) a mixture of a fatty alcohol and a polyoxyethylenated fatty alcohol, or (iii) a mixture of an oil, a fatty alcohol and a polyoxyethylenated fatty alcohol, in the presence of water.

19. The composition of claim 12 in the form of a gel containing a thickener present in an amount ranging from 0.1 to 30 percent by weight based on the total weight of said composition, in the presence of a solvent.

20. A process for protecting the skin and hair against ultraviolet radiation comprising applying to the skin or hair an effective amount of the composition of claim 1.

* * * * *